US009192458B2

(12) United States Patent
Alexander et al.

(10) Patent No.: US 9,192,458 B2
(45) Date of Patent: Nov. 24, 2015

(54) IMPLANTS, TOOLS, AND METHODS FOR TREATMENTS OF PELVIC CONDITIONS (71) Applicant: AMS Research Corporation, Minnetonka, MN (US)

(72) Inventors: James A. Alexander, Excelsior, MN (US); Benjamin Y. Arcand, Minneapolis, MN (US); Chartie Khamis, Edina, MN (US); Daniel Taut, Eden Prairie, MN (US); Thomas O. Viker, Arden Hills, MN (US)

(73) Assignee: AMS Research Corporation, Minnetonka, MN (US)

( * ) Notice: Subject to any disclaimer, the term of this patent is extended or adjusted under 35 U.S.C. 154(b) by 283 days.

(21) Appl. No.: 13/763,296

(22) Filed: Feb. 8, 2013

(65) Prior Publication Data
US 2013/0211193 A1 Aug. 15, 2013

Related U.S. Application Data (60) Provisional application No. 61/596,803, filed on Feb. 9, 2012.

(51) Int. Cl.
| A61F 2/00 | (2006.01) |
| A61B 17/34 | (2006.01) |
| A61B 17/04 | (2006.01) |
| A61B 1/32 | (2006.01) |
| A61B 1/07 | (2006.01) |
| A61B 17/32 | (2006.01) |
| A61B 17/02 | (2006.01) |
| A61B 17/06 | (2006.01) |
| A61B 17/00 | (2006.01) |

(52) U.S. Cl.
CPC .............. *A61F 2/0063* (2013.01); *A61B 17/04* (2013.01); *A61B 17/0401* (2013.01); *A61B 17/3468* (2013.01); *A61B 1/07* (2013.01); *A61B 1/32* (2013.01); *A61B 17/0293* (2013.01); *A61B 17/06166* (2013.01); *A61B 2017/00004* (2013.01); *A61B 2017/0409* (2013.01); *A61B 2017/0414* (2013.01); *A61B 2017/0427* (2013.01); *A61B 2017/0464* (2013.01); *A61B 2017/320056* (2013.01); *A61F 2/0045* (2013.01)

(58) Field of Classification Search
CPC ....................... A61B 17/42; A61B 2017/00876; A61B 17/00234; A61F 2/0045; A61F 2/0063
USPC ................. 600/29–31, 37; 606/139–158, 232
See application file for complete search history.

(56) References Cited

U.S. PATENT DOCUMENTS

| 2,738,790 | A | 3/1956 | Todt et al. |
| 3,124,136 | A | 3/1964 | Usher |
| 3,311,110 | A | 3/1967 | Singerman et al. |
| 3,580,313 | A | 5/1971 | McKnight |
| 3,763,860 | A | 10/1973 | Clarke |
| 3,858,783 | A | 1/1975 | Kapitanov et al. |
| 3,995,619 | A | 12/1976 | Glatzer |
| 4,037,603 | A | 7/1977 | Wendorff |
| 4,128,100 | A | 12/1978 | Wendorff |
| 4,172,458 | A | 10/1979 | Pereyra |
| 4,235,238 | A | 11/1980 | Ogiu et al. |
| 4,246,660 | A | 1/1981 | Wevers |
| 4,441,497 | A | 4/1984 | Paudler |
| 4,509,516 | A | 4/1985 | Richmond |
| 4,775,380 | A | 10/1988 | Seedhom et al. |
| 4,865,031 | A | 9/1989 | O'Keeffe |
| 4,873,976 | A | 10/1989 | Schreiber |
| 5,085,661 | A | 2/1992 | Moss |
| 5,149,329 | A | 9/1992 | Richardson |
| 5,188,636 | A | 2/1993 | Fedotov |
| 5,209,756 | A | 5/1993 | Seedhom et al. |
| 5,256,133 | A | 10/1993 | Spitz |
| 5,269,783 | A | 12/1993 | Sander |
| 5,281,237 | A | 1/1994 | Gimpelson |
| 5,337,736 | A | 8/1994 | Reddy |
| 5,362,294 | A | 11/1994 | Seitzinger |
| 5,368,595 | A | 11/1994 | Lewis |
| 5,370,650 | A | 12/1994 | Tovey et al. |
| 5,376,097 | A | 12/1994 | Phillips |
| 5,413,598 | A | 5/1995 | Moreland |

(Continued)

FOREIGN PATENT DOCUMENTS

| AU | 2002241673 | 11/2005 |
| CA | 2404459 | 8/2005 |

(Continued)

OTHER PUBLICATIONS

Diana et al., "Treatment of vaginal vault prolapse with abdominal sacral colpopexy using prolene mesh," Am. J. of Surgery, vol. 179, pp. 126-128 (2000).

Farnsmorth, B. N., Posterior intravaginal slingplasty (infracoccygeal sacropexy) for severe posthysterectomy vaginal vault prolapse—a preliminary report on efficacy and safety, Int. Urogynecol. J. (2002) 13:4-8.

Visco, et al., "Vaginal mesh erosion after abdominal sacral colpopexy," Am. J. Obstet. Gynecol., vol. 184, No. 3, pp. 297-303 (2001).

*Primary Examiner* — John Lacyk
(74) *Attorney, Agent, or Firm* — Kagan Binder, PLLC (57) ABSTRACT

Described are various embodiments of surgical procedures, systems, implants, devices, tools, and methods, useful for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the devices and tools including devices and tools for anchoring an implant to tissue.

4 Claims, 5 Drawing Sheets

(56) References Cited

U.S. PATENT DOCUMENTS

| | | |
|---|---|---|
| 5,520,700 A | 5/1996 | Beyar et al. |
| 5,520,703 A | 5/1996 | Essig et al. |
| 5,527,342 A | 6/1996 | Pietrzak et al. |
| 5,591,206 A | 1/1997 | Moufarrege |
| 5,628,756 A | 5/1997 | Barker, Jr. et al. |
| 5,683,349 A | 11/1997 | Makower et al. |
| 5,709,708 A | 1/1998 | Thal |
| 5,807,403 A | 9/1998 | Beyar et al. |
| 5,842,478 A | 12/1998 | Benderev et al. |
| 5,919,232 A | 7/1999 | Chaffringeon et al. |
| 5,922,026 A | 7/1999 | Chin |
| 5,944,732 A | 8/1999 | Raulerson et al. |
| 5,972,000 A | 10/1999 | Beyar et al. |
| 6,048,351 A | 4/2000 | Gordon et al. |
| 6,071,290 A | 6/2000 | Compton |
| 6,074,341 A | 6/2000 | Anderson et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,117,067 A | 9/2000 | Gil-Vernet |
| 6,168,611 B1 | 1/2001 | Risvi |
| 6,200,330 B1 | 3/2001 | Benderev et al. |
| 6,328,744 B1 | 12/2001 | Harari et al. |
| 6,387,041 B1 | 5/2002 | Harari et al. |
| 6,482,214 B1 | 11/2002 | Sidor, Jr. et al. |
| 6,530,943 B1 | 3/2003 | Hoepffner et al. |
| 6,575,897 B1 | 6/2003 | Ory |
| 6,582,443 B2 | 6/2003 | Cabak et al. |
| 6,592,515 B2 | 7/2003 | Thierfelder |
| 6,599,323 B2 | 7/2003 | Melican et al. |
| 6,602,260 B2 | 8/2003 | Harari et al. |
| 6,612,977 B2 | 9/2003 | Staskin |
| 6,638,284 B1 | 10/2003 | Rousseau et al. |
| 6,648,921 B2 | 11/2003 | Anderson |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,884,212 B2 | 4/2005 | Thierfelder et al. |
| 6,911,003 B2 | 6/2005 | Anderson et al. |
| 6,936,052 B2 | 8/2005 | Gellman et al. |
| 6,953,428 B2 | 10/2005 | Gellman et al. |
| 6,971,986 B2 | 12/2005 | Staskin et al. |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,558 B2 | 7/2006 | Gellman et al. |
| 7,083,637 B1 | 8/2006 | Tannhauser |
| 7,087,065 B2 | 8/2006 | Ulmsten et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,226,407 B2 | 6/2007 | Kammerer |
| 7,229,404 B2 | 6/2007 | Bouffier |
| 7,229,453 B2 | 6/2007 | Anderson |
| 7,235,043 B2 | 6/2007 | Gellman et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,637,860 B2 | 12/2009 | MacLean |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,766,926 B2 | 8/2010 | Bosley et al. |
| 7,981,024 B2 | 7/2011 | Levy |
| 8,491,460 B1 * | 7/2013 | Montgomery, III ............ 600/37 |
| 2002/0007222 A1 | 1/2002 | Desai |
| 2002/0028980 A1 | 3/2002 | Thierfelder et al. |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0010929 A1 | 1/2003 | Prieve et al. |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0278037 A1 | 12/2005 | Delorme et al. |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0229596 A1 | 10/2006 | Weiser et al. |
| 2007/0078295 A1 | 4/2007 | Landgrebe |
| 2008/0039678 A1 | 2/2008 | Montpetit et al. |
| 2008/0140218 A1 | 6/2008 | Staskin et al. |
| 2008/0300607 A1 | 12/2008 | Meade et al. |
| 2009/0005634 A1 | 1/2009 | Rane |
| 2009/0012353 A1 | 1/2009 | Beyer |
| 2009/0221868 A1 | 9/2009 | Evans |
| 2010/0179575 A1 | 7/2010 | Von Pechmann et al. |
| 2010/0261950 A1 | 10/2010 | Lund |
| 2010/0280627 A1 | 11/2010 | Hanes, II |
| 2011/0082370 A1 * | 4/2011 | Ducharme et al. ............ 600/437 |
| 2011/0124954 A1 | 5/2011 | Ogdahl et al. |
| 2011/0174313 A1 | 7/2011 | Von Pechmann et al. |
| 2012/0016185 A1 | 1/2012 | Sherts et al. |

FOREIGN PATENT DOCUMENTS

| | | |
|---|---|---|
| DE | 19544162 | 4/1997 |
| EP | 0643945 A2 | 7/1994 |
| EP | 0632999 A1 | 1/1995 |
| EP | 1060714 A3 | 9/2002 |
| FR | 2852813 A1 | 1/2004 |
| IT | 1299162 | 4/1998 |
| WO | WO9317635 A1 | 9/1993 |
| WO | WO9525469 A1 | 9/1995 |
| WO | WO9730638 A1 | 8/1997 |
| WO | WO9747244 A1 | 12/1997 |
| WO | WO9835606 A1 | 8/1998 |
| WO | WO9842261 A1 | 10/1998 |
| WO | WO9916381 A1 | 4/1999 |
| WO | WO9952450 A1 | 10/1999 |
| WO | WO0064370 A1 | 2/2000 |
| WO | WO0057812 A1 | 10/2000 |
| WO | WO0074633 A2 | 12/2000 |
| WO | WO0106951 A1 | 2/2001 |
| WO | WO0139670 A1 | 6/2001 |
| WO | WO0156499 A1 | 8/2001 |
| WO | WO0234124 A2 | 5/2002 |
| WO | WO02071953 A2 | 9/2002 |

(56) References Cited

FOREIGN PATENT DOCUMENTS

| | | |
|---|---|---|
| WO | WO02078552 A1 | 10/2002 |
| WO | WO03017848 A1 | 3/2003 |
| WO | WO03003778 A1 | 4/2003 |
| WO | WO03028585 A2 | 4/2003 |
| WO | WO03037215 A2 | 5/2003 |
| WO | WO03041613 A1 | 5/2003 |
| WO | WO03068107 A1 | 8/2003 |
| WO | WO03092546 A2 | 11/2003 |
| WO | WO03096929 A1 | 11/2003 |
| WO | WO2004012626 A1 | 2/2004 |
| WO | WO2005079702 A1 | 9/2005 |
| WO | WO2005122954 A1 | 12/2005 |
| WO | WO2006108145 A1 | 10/2006 |
| WO | WO2007011341 A1 | 1/2007 |
| WO | WO2007016083 A1 | 2/2007 |
| WO | WO2007027592 A2 | 3/2007 |
| WO | WO2007081955 A1 | 7/2007 |
| WO | WO2007097994 | 8/2007 |
| WO | WO2007146784 A2 | 12/2007 |
| WO | WO2007149348 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |
| WO | WO2011/082350 | 7/2011 |

* cited by examiner

IMPLANTS, TOOLS, AND METHODS FOR TREATMENTS OF PELVIC CONDITIONS

CROSS REFERENCE TO RELATED APPLICATION

This application claims the benefit under 35 U.S.C. §119(e) of U.S. Provisional Patent Application No. 61/596,803, filed Feb. 9, 2012 and titled "Implants, Tools, and Methods for Treatments of Pelvic Conditions", which is incorporated herein by reference in its entirety.

TECHNICAL FIELD

The present invention relates generally to implants, tools, devices, systems, apparatus, and related methods for treating pelvic conditions including but not limited to incontinence and prolapse conditions in men and women.

BACKGROUND

Pelvic health for men and women is a medical area of increasing importance, at least in part due to an aging population. Examples of common pelvic ailments include incontinence (e.g., urinary or fecal), pelvic tissue prolapse (e.g., female vaginal prolapse), and conditions of the pelvic floor. Urinary incontinence can further be classified as including different types, such as stress urinary incontinence (SUI), urge urinary incontinence, mixed urinary incontinence, among others. Urinary incontinence can be characterized by the loss or diminution in the ability to maintain the urethral sphincter closed as the bladder fills with urine. Male or female stress urinary incontinence (SUI) generally occurs when the patient is physically stressed. Other pelvic floor disorders include cystocele, rectocele, enterocele, and prolapse such as anal, uterine and vaginal vault prolapse. Pelvic disorders such as these can result from weakness or damage to normal pelvic support systems.

In its severest forms, vaginal vault prolapse can result in the distension of the vaginal apex outside of the vagina, and is often associated with a rectocele, cystocele or enterocele. An enterocele is a vaginal hernia in which the peritoneal sac containing a portion of the small bowel extends into the rectovaginal space. Vaginal vault prolapse and enterocele represent challenging forms of pelvic disorders for surgeons. One known method of repairing vaginal vault prolapse is by suturing to the supraspinous ligament or attaching the vaginal vault through mesh or fascia to the sacrum. Many patients suffering from vaginal vault prolapse also require a surgical procedure to correct stress urinary incontinence that is either symptomatic or latent. Many of these procedures often involve lengthy surgical procedure times.

There is therefore a desire to provide minimally invasive yet highly effective implantable systems that can be used to treat incontinence, and/or pelvic organ prolapse and other conditions. It is further desirable that such systems can be delivered via minimally invasive (e.g., transvaginal, laporoscopic, transabdominal) surgical procedures.

SUMMARY

Devices, systems, and methods as described can be used to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), levator defects, and other conditions caused by muscle and ligament weakness, hysterectomies and the like. While many of the surgical procedures and devices described herein are directed to transvaginal surgical procedures, it is understood that the procedures can instead be performed using laparoscopic and/or transabdominal approaches.

One procedure that can be used to treat vaginal prolapse conditions is sacral colpopexy. An aspect of certain sacral colpopexy procedures is to place a fixation element (e.g., an anchor such as a bone anchor or soft tissue anchor) into tissue of a posterior pelvic region to secure an implant to the tissue. This aspect of the procedure requires a surgeon to place a tissue anchor at a location deep inside a posterior pelvic region, such as through a transvaginal incision (when using certain current methods).

Surgical tools and procedural improvements are disclosed herein. Certain embodiments of tools and methods are used for attaching sutures, mesh, or other devices to the anatomy, such as for treating incontinence and/or prolapse. Embodiments of the tools can be used for deploying sutures through a retractor and into the peritoneum, for example. This can be useful for a number of different procedures that require suturing in the peritoneal space, such as sacral colpopexy (e.g., for attaching mesh material to the sacral promontory and for closing the peritoneal membrane over the mesh), high uterosacral suspension procedures (e.g., for passing suture through a tissue structure and fixating the suture to that tissue structure), McCall culdoplasty (i.e., a method of supporting the vaginal cuff by attaching the uterosacral and cardinal ligaments to the peritoneal surface with suture material that can be drawn toward the midline to help close off the cul-de-sac), uterosacral suspension procedures, and the like.

Various surgical tools, implants, and procedural improvements are disclosed herein. Certain embodiments of methods and implants involve reperitonealization or covering sacral mesh during a transvaginal sacrocolpopexy procedure using a curved trocar and retractor system. Certain embodiments of methods and implants described herein involve placing a fixation element at the sacrum and then attaching mesh to the fixation elements via a snapping or other positive engagement system. Other methods, devices, and systems provided herein include a suture knot pusher, a clip-on light tube for use with a surgical transvaginal sacrocolpopexy retractor, a method of moving the bowel out of the retractor and the physician's view, a vaginal mesh suture pad and instrument, suction tip features at the end of a retractor, and a retractor with flexible fingers at one end. Embodiments of implants and methods can involve placement of an implant to support pelvic tissue, by way of one or more incisions of minimum size, for example.

BRIEF DESCRIPTION OF THE DRAWINGS

The invention will be further explained with reference to the appended Figures, wherein like structure is referred to by like numerals throughout the several views, and wherein.

DETAILED DESCRIPTION

Pelvic floor disorders include cystocele, rectocele, enterocele, and uterine and vaginal vault prolapse, levator defects, among others, in male and female patients. These disorders typically result from weakness or damage to normal pelvic support systems. The most common etiologies include childbearing, removal of the uterus, connective tissue defects, prolonged heavy physical labor and postmenopausal atrophy.

Vaginal vault prolapse is the distension of the vaginal apex, in some cases to an orientation outside of the vagina. Vaginal vault prolapse is often associated with a rectocele, cystocele or enterocele. It is known to repair vaginal vault prolapse by suturing the vaginal vault (e.g., by stitches) to the supraspinous ligament or by attaching the vaginal vault through mesh or fascia to the sacrum. Many patients suffering from vaginal vault prolapse also require a concurrent or subsequent surgical procedure to correct stress urinary incontinence that is either symptomatic or latent.

In order to place a sling to stabilize or support the bladder neck or urethra, such as for the treatment of incontinence, surgical procedures and devices are often used. There are a variety of different sling procedures, where the slings used for pubovaginal procedures vary widely in the types of material and anchoring methods. In some cases, the sling is placed under the bladder neck and secured via suspension sutures to a point of attachment (e.g., bone) through an abdominal and/or vaginal incision. Examples of sling procedures are disclosed, for example, in U.S. Pat. Nos. 5,112,344; 5,611,515; 5,842,478; 5,860,425; 5,899,909; 6,039,686; 6,042,534; and 6,110,101.

A sacral colpopexy (otherwise known as "sacrocolpopexy") is one procedure used for providing vaginal vault suspension. It may be performed through an abdominal incision, a vaginal incision, or laparoscopically. A sacral colpopexy entails suspension (by use of an implant such as a strip of mesh) of the vaginal cuff to a region of sacral anatomy such as the sacrum (such as may be accomplished using bone screws that are implanted into the sacrum), a nearby sacrospinous ligament, uterosacral ligament, or anterior longitudinal ligament at the sacral promontory. An implant such as a synthetic mesh can be carefully customized or assembled into a special shape by the surgeon. In some sacral colpopexy procedures that also involve a hysterectomy, an implant can alternatively be attached to posterior vaginal tissue that remains after removal of the uterus and cervix, and also to anatomy to support the vaginal tissue at or around the sacrum, such as to uterosacral ligaments or to the sacrum itself (i.e., to a component of the sacral anatomy).

As used herein, the term "anchor" refers non-specifically to any structure that can connect an implant to tissue of a pelvic region. The tissue may be bone, or a soft tissue such as a muscle, fascia, ligament, tendon, or the like. The anchor may be any known or future-developed structure, or a structure described herein, useful to connect an implant to such tissue, including but not limited to a clamp, a suture, a soft tissue anchor such as a self-fixating tip, a bone anchor, any of the structures described herein to be useful to connect an implant to soft tissue or bone of a pelvic region, or the like.

The suturing instruments described herein are directed to the surgical treatment of a pelvic condition including prolapse (e.g., any form of vaginal prolapse), urinary and fecal incontinence, levator defects, etc., in a male or female patient. To treat such conditions, one or more implants can be implanted in a male or a female to treat a condition such as urge incontinence, mixed incontinence, overflow incontinence, functional incontinence, and the like. To treat any of such conditions, one or more implants can be implanted in a male or a female, which implants can include a tissue support portion that can be used to support a urethra or other pelvic tissue, along with one or more extension portions (otherwise known as an end portion or arm) attached or attachable to the tissue support portion. An implant may include portions, pieces, or sections that are synthetic or made of biologic material (e.g., porcine, cadaveric, etc.). Extension portions of an implant may be a synthetic mesh, for example, such as a polypropylene mesh, a suture, a biodegradable suture, etc. The tissue support portion may be synthetic (e.g., a polypropylene mesh) or biologic. Examples of implant products that may be similar to those useful according to the present description, include those sold commercially by American Medical Systems, Inc., of Minnetonka Minn., under the trade names "Apogee", "Perigee", and "Elevate" for use in treating pelvic prolapse (including vaginal vault prolapse, cystocele, enterocele, etc.), and under the trade names "Sparc", "Bioarc", "Monarc", "MiniArc", "InVance", and "AdVance" for treating urinary incontinence.

In exemplary uses, extension portions of an implant can extend from the location of attachment with the tissue support portion, through pelvic tissue, and optionally be attached to supportive tissue within the pelvic region. For certain procedures, the supportive tissue can be tissue adjacent to the urethra such as pelvic fascia; tissue between the urethra and an obturator foramen such as pelvic fascia; or tissue of an obturator foramen such as obturator fascia, obturator internus muscle, obturator membrane, obturator externus muscle, etc. For alternate procedures an extension portion can be sized to extend from the tissue support portion, through an obturator foramen, around a pubic ramus bone, and threaded (subcutaneously) back to a medial location such as near a medial incision.

Implants as described can include a tissue fastener at a distal end or a distal portion of an extension portion, which is the end or portion not attached to a tissue support portion. As used herein, the term "distal" generally refers to a direction toward a patient and away from a surgeon installing a device. A tissue fastener at a distal end or portion of an extension portion can be any of various types, including: a self-fixating tip that is inserted into soft tissue and frictionally retained;

soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120; U.S. patent application Ser. Nos. 12/223,846 and 12/669,099; and WO 2009/075800, the entireties of which are all incorporated herein by reference). An implant may also have one or more extension portions that do not include a tissue fastener, such as may be used if the distal end is designed to be secured to tissue by other methods (e.g., suturing), or is intended to pass through an obturator foramen and a tissue path around a pubic ramus bone, in which case the extension portion may optionally include a connector, dilator, or dilating connector, which connects to an elongate tool that can be used to either push or pull the connector, dilator, or dilating connector through a tissue path (e.g., to a medial incision).

One embodiment of a tissue fastener is a self-fixating tip. In general, a self-fixating tip can be a structure (sometimes referred to as a soft tissue anchor) connected at a distal end of an extension portion (or extension portion piece) that can be implanted into soft tissue (e.g., muscle, fascia, ligament, etc.) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through a medial incision to reach the interior of the pelvic region, e.g., at a location of an obturator foramen.

According to various systems, one or more instruments, insertion tools, adjusting tools, or the like, may be incorporated or used with an implant or method as described. Examples of useful tools include those that generally include one or more (stationary or moveable) thin elongate, relatively rigid shafts or needles that extend from a handle. The shaft can be a single elongate shaft or multiple separate elongate shafts extending from the handle, or one or more primary shafts that extend from the handle and that contain multiple branch or "tine" shafts that separate at the end of the primary shaft. The handle is located at a proximal end of the device and attaches to one end (a proximal end) of a shaft. According to some embodiments, a distal end of one or more shafts can be adapted to engage a portion of an implant, such as a tissue fastener (e.g., a self-fixating tip), in a manner that allows the insertion tool to engage and push the tissue fastener through a tissue passage and connect the tissue fastener to supportive tissue of the pelvic region. Examples of this type of tool can be used with a self-fixating tip that includes an internal channel designed to be engaged by a distal end of an insertion tool to allow the self-fixating tip to be pushed into tissue. Other general types of insertion tools will also be useful, but may engage a self-fixating tip or other tissue fastener in an alternate manner, e.g., that does not involve an internal channel.

Exemplary insertion tools for treatment of incontinence and vaginal prolapse are described, e.g., in U.S. patent application Ser. Nos. 10/834,943; 10/306,179; 11/347,553; 11/398,368; and 10/840,646; PCT Application Nos. 2006/028828 and 2006/0260618; WO 2010/093421; and U.S. Patent Publication No. US 2010/0256442, wherein the entirety of these documents are incorporated herein by reference. A tool that can be used for embodiments of the invention can optionally include a mechanism by which a tissue fastener (e.g., a self-fixating tip) can be securely and releasable engaged with a distal end of an insertion tool such that the tissue fastener can be selectively secured to the distal end mechanically, then selectively released. With a releasable engagement, a tissue fastener (e.g., self-fixating tip) can be released from the distal end by releasing the engagement (e.g., mechanical engagement) by movement of an actuator at the proximal end of the insertion tool, such as at the handle. Optionally, an implant can include a tissue fastener at a location of a tissue support portion, or at a location along a length of an extension portion. This form of tissue fastener can be in the form of reinforced (e.g., by coating, heat treating, or a reinforcing weave or strip) edge extensions, multiple layers of mesh and edge extensions in an extension portion, etc., as described, for example, at Applicant's copending U.S. Pat. No. 7,422,557, and Applicant's copending United States Patent Publication Nos. US 2006/0195011, US 2006/0195007, and US 2006/0195010, all of which are incorporated herein by reference.

Figure 1:
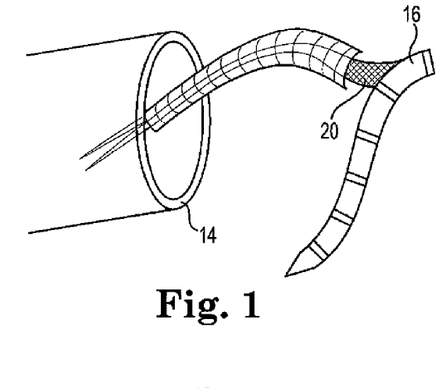
FIG. 1 is a schematic perspective view of a surgical procedure for reperitonealizing sacral mesh.
Figure 2:
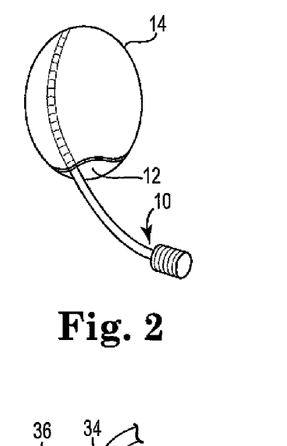
FIG. 2 is a schematic front view of a trocar tunneling under the peritoneum in the area of the vaginal cuff and to the sacral promontory of a patient.
Figure 3:
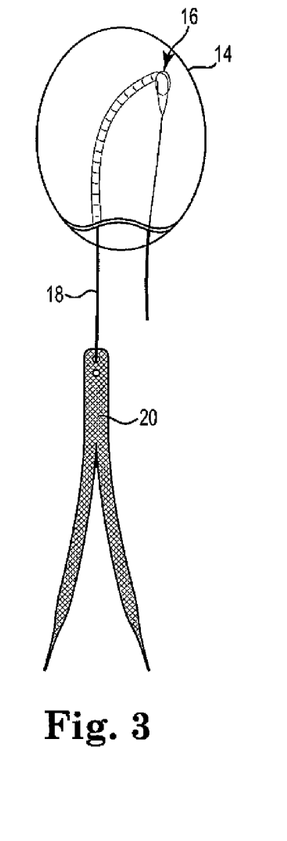
FIG. 3 is another schematic view of the arrangement of FIG. 2, and further illustrating a mesh member connected via a suture.

Referring now to the Figures, and initially to FIGS. 1 through 3, a method and device are illustrated for reperitonealizing sacral mesh as part of a sacrocolpopexy procedure. Reperitonealization or covering of the mesh inside the peritoneal cavity can be important for avoiding complications such as bowel obstruction, infection, bowel adhesions, and the like. In many known surgical methods, reperitonealization has been accomplished by cutting the peritoneal membrane and suturing it back over the mesh, which approach can be relatively difficult to accomplish when using a transvaginal approach. The method of the present invention, however, provides an alternative approach to reperitonealization by tunneling under the peritoneal membrane in order to separate the sacral mesh from the bowel.

In accordance with the invention, a curved trocar 10 is provided with a retractor system. The trocar 10 is introduced through a small pocket 12 that is created at the open vaginal cuff 14 between the vaginal musosa and the peritoneal membrane. The trocar 10 is advanced under the peritoneal membrane and toward the sacral promontory 16 along the right pelvic sidewall of the patient. The movement or advancement of the trocar 10 can be monitored using a retractor, which is used to clear the small bowel off the peritoneum and gain direct visual access to the peritoneal membrane and a tip of the trocar 10. This advancement or tunneling of the trocar 10 can be continued all the way to the sacral promontory 16 where an incision has been made through the peritoneal membrane. When the trocar 10 reaches the sacral promontory 16 and can be seen through the peritoneal incision, a suture 18 can be loaded onto the tip of the trocar 10, and the trocar 10 can be pulled out with the suture 18. The suture 18 can be of a sufficient length that it will extend from the introitus through the peritoneal tunnel and back to the introitus, as is illustrated in FIG. 3 (e.g., with a suture loop). The tunnel under the peritoneal membrane can be used for pulling a sacral mesh 20 though the patient until it reaches the sacrum, to which it can be attached. In particular, one end of the suture 18 can be tied to the sacral mesh 20 and pulled through the peritoneal tunnel. In one exemplary embodiment, two fixation elements (not shown) will have been fixated at the sacral promontory 16 so that the sacral mesh 20 can be snapped or otherwise connected to these fixation elements. When this is done, the reperitonealization aspect of the transvaginal colopopexy procedure can be considered to be complete.

Figure 4:
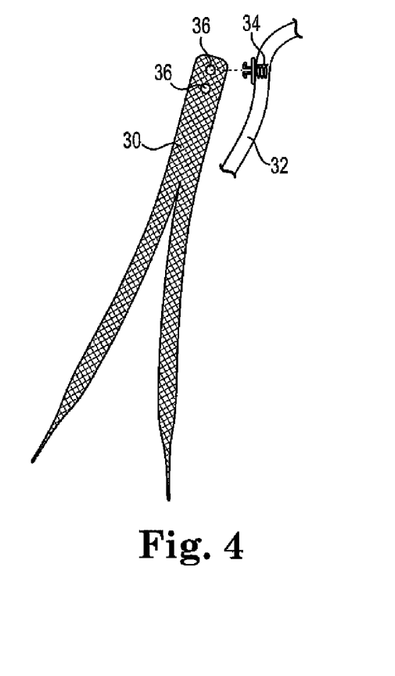
FIG. 4 is a schematic view of a manner of connecting a mesh member to a sacral promontory.

In at least one currently used surgical method, a fixating element and a mesh are both loaded on a fixation driver that is used for placing the fixation element at the sacral promontory. Due to the presence of mesh at the tip of the driver, this method can be cumbersome and can therefore cause difficulty in achieving accurate placement of the fixation element at the sacral promontory. Because accurate placement of the fixation element is important for avoiding critical structures at the sacrum, there is a need to provide different methods and/or instruments for these surgical methods. FIG. 4 illustrates one such exemplary method of attaching a mesh member 30 to a sacral promontory 32, such as during a transvaginal sacrocolpopexy procedure. With this method, one or more fixation elements 34 are implanted separately from the mesh member 30 during fixation delivery by first attaching the fixation element(s) 34 at desired locations at the sacral promontory 32, such as by screwing the fixation elements 34 into the sacrum, for example. The mesh member 30 can then be attached or "snapped" the onto the fixation element(s) 34. For one example, a fixation element 34 can be connected to the sacral promontory 32 in the area of the anterior ligament, while the mesh member 30 is provided with an end portion having one or more eyelet-type elements 36 that are designed for engaging with this fixation element 34. In one embodiment, the attachment of an eyelet 36 to a fixation element 34 is accomplished by pressing an eyelet element 36 onto one of the fixation elements 34 until the eyelet element 36 snaps or otherwise attaches to the fixation element 34. The mesh member 30 can alternatively or additionally be provided with a different type of attachment element than the eyelet-type element, wherein such an attachment element can be designed or selected for secure attachment to a structure or portion of a fixation element. With this method, it is contemplated that two or more fixation elements can be snapped or otherwise attached to a single mesh member, if desired.

Figure 5:
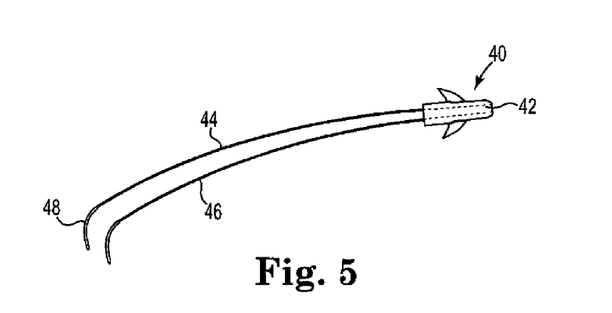
FIG. 5 is a front view of an exemplary embodiment of a fixation kit or system.
Figure 6:
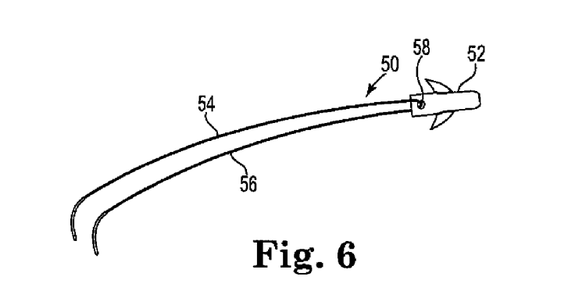
FIG. 6 is a front view of another exemplary embodiment of a fixation kit or system.
Figure 7:
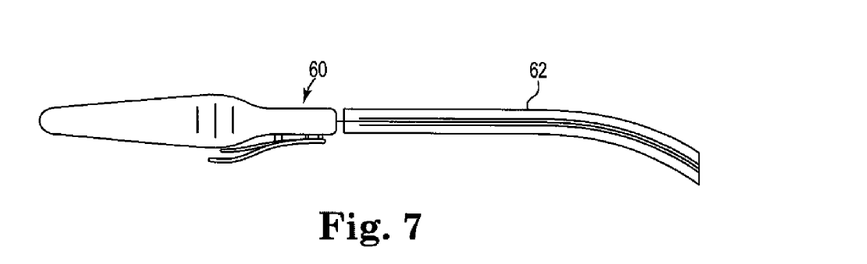
FIG. 7 is a front view of another exemplary embodiment of a fixation kit or system.

In accordance with another aspect of the invention, which is generally illustrated in FIGS. 5 through 7, for example, a kit is provided that can be used in sacrospinous ligament suspension procedures. In other words, such a fixation kit is provided for the sacrospinous ligament/uterosacral/soft tissue. This fixation kit leverages the prolapse repair and cystocele treatment system recognized under the trade name "Elevate", which is commercially available from American Medical Systems of Minneapolis, Minn. The kit includes a fixation element similar to that used with the "Elevate" system, along with two suture threads that are securely attached to the fixation element. The attachment of the suture threads to the fixation element can be accomplished in a number of different ways, such as through a molding process, by looping suture thread(s) through an eyelet on the fixation element, or by tying the suture thread(s) to an eyelet on the fixation element. The kit also includes an instrument that can be used for delivering the fixation element and sutures or thread into the ligament. This kit may include an element that is similar to the apical needle used for the "Elevate" system, with or without modifications to accommodate the sutures.

With particular reference to FIG. 5, an exemplary fixation kit or system 40 is provided, which includes a fixation element 42 into which two sutures 44, 46 are molded or otherwise attached. The sutures 44, 46 may be made from a variety of materials, such as permanent or reabsorbable polymers, for example. The sutures 44, 46 can be positioned within the fixation element 42 by any desired distance and/or configuration that will securely attach the components to each other so that the sutures will not become prematurely disengaged from the fixation element. The kit or system 40 may further include a needle 48 at an end of one or both of the sutures 44, 46 that is opposite the end that is attached to the fixation element 42. These needle(s) 48 can help with passing through vaginal tissue.

FIG. 6 illustrates another exemplary fixation kit or system 50 that includes a fixation element 52 having an eyelet 58 at one end to which one or more sutures or suture segments 54, 56 are attached. In one embodiment, a single suture is looped through the eyelet 58, and in another embodiment, two sutures are attached to the eyelet 58 or to another area of a base of the fixation element 52, such as by tying each of the sutures to the eyelet 58. If a single suture is looped through the eyelet 58, the suture may be inserted into the eyelet so that it is free to move along its length relative to the eyelet, which can be advantageous for certain surgical procedures, or the suture can instead be secured to the eyelet itself so that it cannot be moved relative to the eyelet along its length.

Another exemplary fixation kit 60 is illustrated in FIG. 7. Fixation kit 60 includes an apical needle assembly of the type that can be used for the Elevate system discussed above. This system further includes a sheath 62 that can have provisions for facilitating management of sutures and/or needles.

Figure 8:
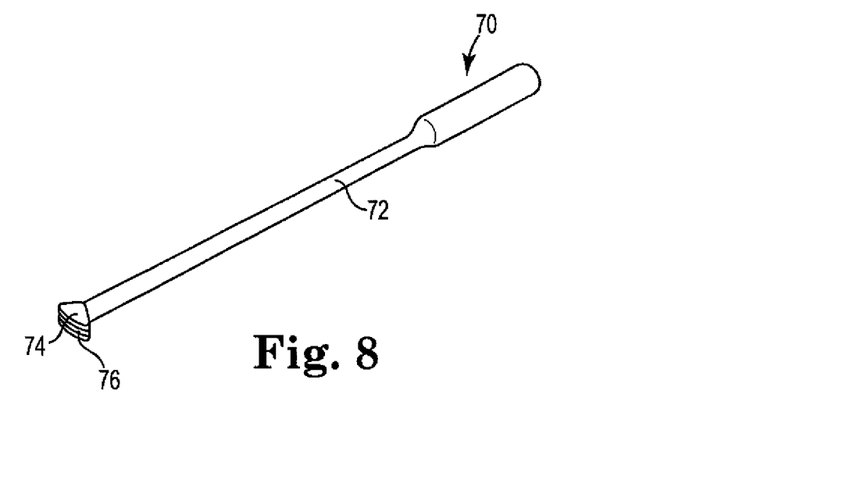
FIG. 8 is a perspective view of a suture knot pusher device.

FIG. 8 illustrates an exemplary suture knot pusher 70 that can be used in accordance with a number of the methods and systems described herein, along with other surgical procedures. Suture knot pusher 70 includes an elongated member 72 and a distal end portion 74 that extends from a distal end of the elongated member 72. The distal end portion 74 is shown as having a width that is larger than the width or diameter of the elongated member 72, and can have a wide variety of shapes and sizes. In this illustrated embodiment, the distal end portion 74 includes a tapered shape with a width that increases from the point where it extends from the elongated member 72. The distal end portion 74 includes a saddle shaped end with an embedded groove 76. The groove 76 is designed to hold one or more sutures or suture segments so that the suture(s) can be pushed along a pathway that would otherwise be difficult to access with the hands, such as through a retractor, for example. The saddle shape of the groove 76 allows the suture lines to be pulled at a number of angles, including at approximately right angles to the direction that the suture and pusher 70 are being translated or "pushed". Pulling on the opposing lines can cause the knot to advance in the direction that the pusher 70 is being moved or translated.

Figure 9:
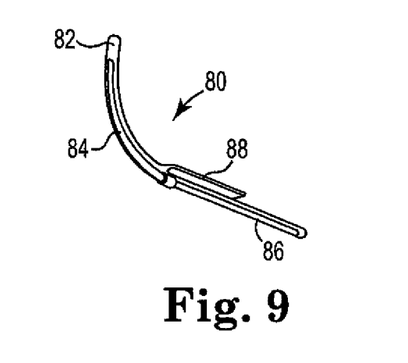
FIG. 9 is a perspective view of a system for attaching a light cable to a retractor.
Figure 10:
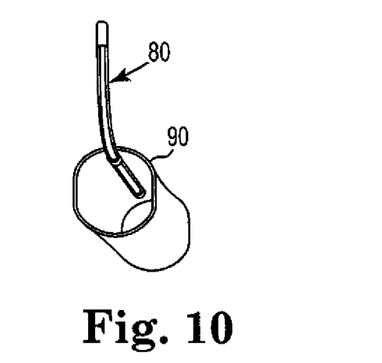
FIG. 10 is a perspective view of the system of FIG. 9 as it can be attached to a retractor tube.

FIGS. 9 and 10 illustrate a system that can be used for attaching a light cable to a retractor in order to direct light to a specific surgical site at the end of a retractor. In this exemplary embodiment, a clip-on light tube or light pipe 80 is illustrated that includes a frame 82, which may be made of plastic or another relatively rigid material, for example, although the frame 82 may have at least a small amount of flexibility. The frame 82 supports an optical fiber 84 that extends along at least a portion of its length. Alternatively, a frame and optical fiber may be integrated and molded as a one-piece component, which may be transparent, translucent, or opaque.

One end of the frame 82 may include a bayonet-type fitting, for example, which can be used for connection of a light cable and a light source. Alternatives to the bayonet-type fitting can alternatively be used, such as a threaded connector, friction connection, and the like. The light pipe 80 can further include a tapered dovetail insert 86 at an end of the frame 82 opposite that end that can include the bayonet-type fitting. This insert 86 can include an extending tab 88 that slides into a dovetail slot that is provided on the inner surface of a retractor tube 90, a portion of which is illustrated in FIG. 10. The dovetail attachment can provide a light interference fit between components, with the light pipe 80 being positioned so that it is partially within the retractor tube 90 and partially extending from the retractor tube 90. Alternative attachments are also possible, such as can be provided via components of the light pipe 80 and retractor tube 90 that can be snap-fit, frictionally fit, interference fit, or otherwise attached to each other, for example. With regard to the illustrated tapered dovetail type of connection between components, such a connection method can also be used to attach other devices to the retractor, such as fiber scopes, laparoscopic instruments, irrigation tubes, suction tubes, and the like.

In a sacrocolpopexy procedure, it can be desirable to provide a relatively easy method of accessing the sacral promontory in a minimally traumatic or non-traumatic manner. Exemplary methods of the invention, along with associated devices, are illustrated in FIGS. 11a-11c and 12a-b, which provide for methods of moving the bowel out of the area of a retractor so that it does not block a physician's view of the area. Also contemplated are methods to provide direct visualization of the sacral promontory in order to eliminate blind or partially blocked visual access and confirmation. Other advantages that can be provided by these methods include safe and easy device manipulation, along with a relatively low insertion force for the device.

Figure 11A:
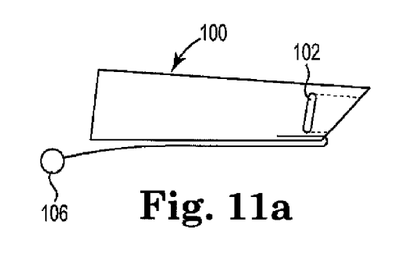
FIGS. 11*a*-11*c* are schematic views of a retractor apparatus for use in a sacrocolpopexy or related procedure.
Figure 11B:
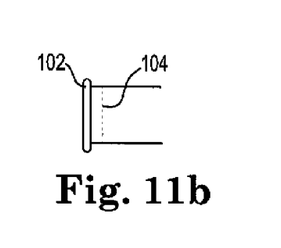
Figure 11C:
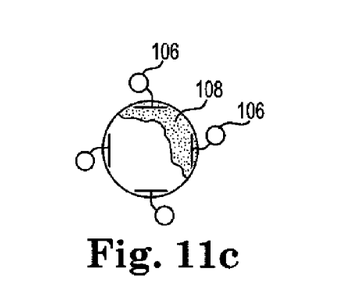

A first exemplary embodiment of an access procedure and device is illustrated and described relative to FIGS. 11a-11c. As illustrated, a retractor tube 100 is provided, which can be provided with an anchor 102 having perforated or "tear away" features, such as the tear away line 104 illustrated best in FIG. 11b. The tube 100 can further be provided with one or more associated pull rings 106 that extend from an elongated member (e.g., a pull cord), wherein four of such rings are shown in FIG. 11c, although it is understood that more or less than four rings may be used. At least some portions of the tube and/or its associated tear away portion(s) and elongated member(s) can be made of can be made of a relatively soft and/or flexible material, such as a mesh, cloth, or plastic material, for example. In operation, the retractor tube 100 is placed in a patient, and if the bowel 108 is in view at the end of an obturator, a corresponding pull ring 106 can be pulled outwardly until the perforated or tear away line 104 breaks. A corresponding movement of the cloth or mesh will move the bowel out of view.

Figure 12A:
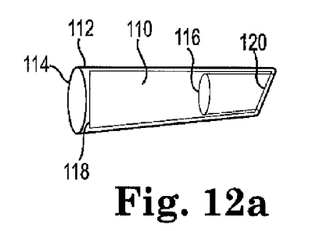
FIGS. 12*a* and 12*b* are front views of a retractor tube with a sleeve.
Figure 12B:
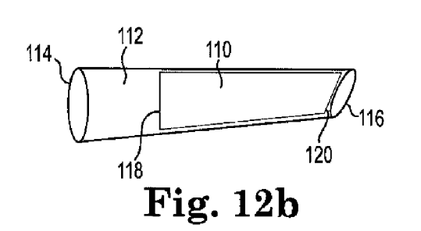

A second exemplary embodiment of an access procedure and device is described relative to FIGS. 12a-b, which is generally configured as an "inverted sock" type of device and procedure. As illustrated in FIG. 12a, a retractor tube 110 is surrounded by a cover 112 that has a first end 114 and a second end 116. As shown, the first end 114 of the cover 112 is adjacent to a first end 118 of the tube 110, and the second end 116 of the cover 112 is inverted over a second end 120 of the tube 110 so that it is positioned within the interior area of the retractor tube 110. The tube 110 with the cover 112 are placed in a patient in this configuration and advanced as far as possible without moving the cover 112. A physician can then look through the tube 110 while pulling on the cover 112 and pushing the tube 110 into the patient, thereby navigating toward the sacral promontory. Once the sacral promontory is reached, the cover 112 is pulled until its second end 116 is no longer within the inner area of the tube 110, but can be adjacent to the second end 120 of the retractor 110, as is illustrated in FIG. 12b. It is noted that pulling of the cover 112 to advance the tube 110 can reduce the required insertion force as compared to a tube 110 that does not have such a cover 112. In addition, the cover 112 can be made of a relatively soft outer material that can help to move and manage the bowel in a relatively atraumatic manner.

Figure 13:
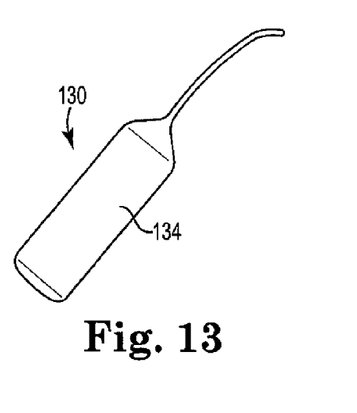
FIG. 13 is a top view of a surgical tool for use during suturing processes.
Figure 14:
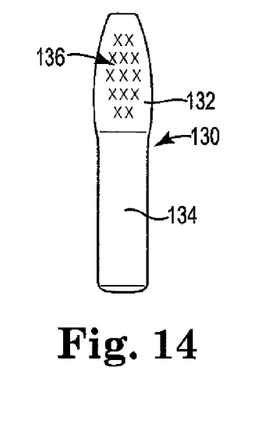
FIG. 14 is a front view of the surgical tool of FIG. 13.
Figure 15:
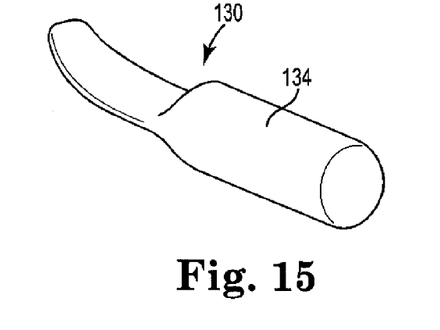
FIG. 15 is a perspective view of the surgical tool of FIGS. 13 and 14.

In some cases, attachment of mesh to the vagina in a sacrocolpopexy procedure can be difficult and time consuming. To address this issue an exemplary tool of the invention is illustrated in FIGS. 13-15, which provides a structure to which a mesh and vagina can be clamped during suturing. In particular, a tool 130 is illustrated that includes a curved flat surface 132 to which the vaginal wall and mesh can be secured, such as with clamps (e.g., Kelly clamps). That is, the mesh and vaginal wall are clamped to a suture pad 136 at the area of the curved flat surface 132, and then the physician can suture the two together while controlling depth and mesh flatness. The tool 130 further includes a handle 134 that can be used to support and manipulate the vaginal wall while suturing. With this tool 130, more controlled suture depth can be achieved to prevent puncturing or capturing unwanted tissue when suturing. In addition, the use of this tool 130 can provide more assurance that the mesh is appropriately sized and that it lies flat during the suturing process.

Figure 16:
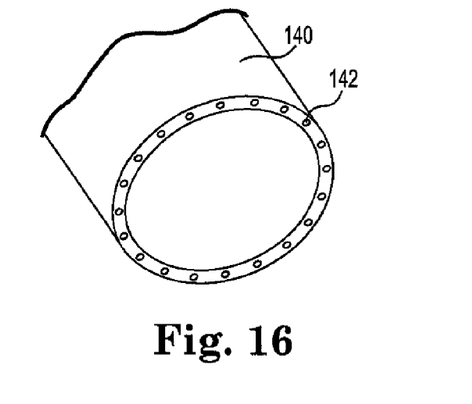
FIG. 16 is a perspective end view of a retractor that includes a plurality of suction holes.

FIG. 16 illustrates an end of an exemplary retractor 140 that includes at least one suction hole 142 that terminates at one of the ends of the retractor 140 (e.g., at a front rim or distal end of the retractor 140). The number, placement, size, shape, and other features of the suction holes 142, and their associated channels that extend through the walls of the retractor 140, can vary widely, and are generally provided to affix the tip of the retractor 140 to the peritoneum over the sacrum. In some cases, this can help to keep the peritoneum taut across the opening of the retractor. In addition, this can help to keep the retractor positioned in a desired location within the patient. A suction device or mechanism can be provided at a proximal end of the retractor for communication with the channels and suction holes 142, wherein such a suction device or mechanism can provide for adjustable suction so that the physician can achieve a desired amount of force between the distal end of the retractor and the peritoneum or other tissue of the patient.

Figure 17:
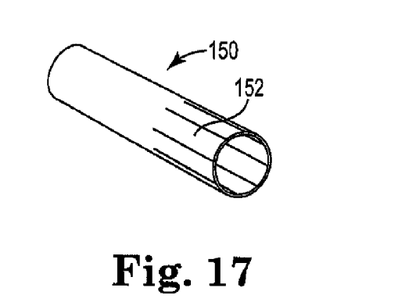
FIG. 17 is a perspective view of an exemplary embodiment of a retractor.
Figure 18:
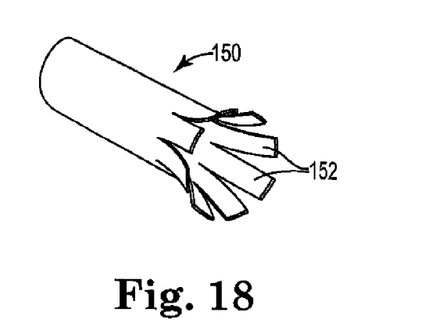
FIG. 18 is another perspective view of the retractor of FIG. 17, wherein the end portion is in an expanded condition.

FIGS. 17 and 18 illustrate an end portion of a retractor 150 that includes a plurality of fingers or flanges 152 extending from a solid length of tubing to an end of the retractor. The fingers or flanges 152 can be formed or created around the perimeter of the retractor by cutting the tube along slit lines in multiple locations, or can alternatively be created by removing thin slots of material from between the fingers 152. The number, length, width and other features of the fingers or flanges 152 can vary widely, and are generally provided to achieve a certain amount of expansion without compromising the capabilities of the retractor during surgery. In surgery, the retractor can be used to move the bowel away from the sacral promontory, where the retractor 150 can be inserted into a patient with the fingers 152 in a non-expanded condition, as is illustrated in FIG. 17, and when it is desired to move structures from each other, the fingers 152 can be expanded or bent outwardly, as is illustrated in FIG. 18. This expansion provides a larger working area for the surgeon.

Suturing instruments described herein can be used for supporting pelvic tissue, and can therefore be useful in conjunction with other methods of treating pelvic conditions, such as treating a levator hiatus, anal incontinence, etc. The implants and tools described herein can be made of conventional materials. For example, the various mesh members and portions can be constructed of polymer materials, such as a thin film or sheet material of polypropylene, polyethylene, fluoropolymers or like compatible materials, both permanent and absorbable, and the suturing instrument components can be made of standard surgical-grade materials, such as polymeric materials, stainless steel, and the like.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the references incorporated herein are envisioned for use with the present invention as well. All patents, patent applications, and publications cited herein are hereby incorporated by reference in their entirety as if individually incorporated, and include those references incorporated within the identified patents, patent applications and publications.

The invention claimed is:

1. A method of reperitonealizing a sacral mesh comprising the steps of:
creating a tunnel under a patient's peritoneal membrane with a curved trocar that is advanced along the right pelvic sidewall of the patient and toward the sacral promontory;
introducing the trocar into the patient through a small pocket that is created at the open vaginal cuff between the vaginal mucosa and the peritoneal membrane;
providing an incision in the peritoneal membrane adjacent the sacral promontory through which the trocar is advanced;
loading a suture onto the trocar and pulling the trocar from the tunnel;
attaching a mesh member to the suture and pulling the mesh member through the tunnel; and
attaching the mesh member to the sacral promontory of the patient.

2. The method of claim 1, further comprising a step of monitoring advancement of the trocar using a retractor system to clear the patient's small bowel off of the patient's peritoneum.

3. The method of claim 1, further comprising the step of attaching at least one fixation element to the sacral promontory.

4. The method of claim 1, further comprising the steps of attaching at least one fixation element to the sacral promontory and then attaching at least one eyelet of the mesh member onto at least one of the fixation elements.

* * * * *